US006379550B1

(12) United States Patent
Chadha et al.

(10) Patent No.: US 6,379,550 B1
(45) Date of Patent: Apr. 30, 2002

(54) METHOD FOR DETECTING PSA AND ITS MOLECULAR FORMS USING THIOPHILIC GEL

(75) Inventors: Kailash C. Chadha, Williamsville; Eugene Sulkowski, Buffalo; Elzbieta Kawinski, Orchard Park, all of NY (US)

(73) Assignee: Health Research, Inc., Buffalo, NY (US)

(*) Notice: Subject to any disclaimer, the term of this patent is extended or adjusted under 35 U.S.C. 154(b) by 71 days.

(21) Appl. No.: 09/624,692

(22) Filed: Jul. 24, 2000

(51) Int. Cl.$^7$ ............................................. B01D 15/08
(52) U.S. Cl. .................. 210/635; 210/656; 210/198.2; 435/7.23; 435/7.4
(58) Field of Search ................. 210/635, 656, 210/659, 198.2; 435/7.23, 7.4; 436/518

(56) References Cited

U.S. PATENT DOCUMENTS

| | | | | |
|---|---|---|---|---|
| 5,543,332 | A | * 8/1996 | Lihme | 436/528 |
| 5,599,677 | A | 2/1997 | Dowell et al. | 435/7.4 |
| 5,654,161 | A | 8/1997 | Tewari | 435/7.23 |
| 5,672,480 | A | 9/1997 | Dowell et al. | 435/7.4 |
| 5,856,182 | A | 1/1999 | Kuus-Reichel et al. | 435/330 |
| 5,912,158 | A | 6/1999 | Lilja et al. | 435/226 |
| 5,928,878 | A | 7/1999 | Allard et al. | 435/71 |
| 5,939,533 | A | 8/1999 | Lilja et al. | 530/387.7 |
| 6,090,559 | A | 7/2000 | Russell et al. | 435/6 |
| 6,100,049 | A | 8/2000 | Luderer et al. | 435/7.4 |
| 6,225,047 | B1 | * 5/2001 | Hutchens | 210/656 |

OTHER PUBLICATIONS

D. Chan, et al. "Prostate–specific Antigen: Advances and Challenges", Clinical Chemistry 45, No. 6, pp. 755–756, 1999.

Z. Chen, et al. "Prostate Specific Antigen in Benign Prostate Hyperplasia: Purification and Characterization", J. Urology, vol. 157, 2166–2170, Jun. 1997.

F. Espana, et al., "Free and Complexed Prostate Specific Antigen in the Differentiation of Benign Prostatic Hyperplasia and Porstate Cancer: Studies in Serum and Plasma Samples", J. Urology, vol. 160, 2081–2088, Dec. 1998.

J. Peter, et al., "Purification of Prostate–Specific Antigen from Human Serum by Indirect Immunosorption and Elution with a Hapten", Analytical Biochemistry, 273, 98–104, 1999.

Y. Qian, et al., "Two–Dimensional Gel Electrophoresis Detects Prostate–Specific Antigen—$_1$–Antichymotrypsin Complex in Serum but not in Prostatic Fluid", Clinical Chemistry, 43:2, 352–359, 1997.

A. Schwarz, et al., "Possible Sites on Antibodies Involved in Thiphilic Adsorption", Advances in Mol. Cell Biology, vol. 15B, pp. 547–551, 1996.

(List continued on next page.)

*Primary Examiner*—Ernest G. Therkorn
(74) *Attorney, Agent, or Firm*—Michael L. Dunn

(57) ABSTRACT

A method for capturing PSA and its molecular forms that may be in a fluid biological material including the steps of: preparing a chromatographic column by placing a thiophilic gel in a column where the thiophilic gel is formed from a water insoluble polymer where the surface of the gel is provided with thiophilic moieties that bind PSA in the presence of an adsorption liquid but that will release PSA upon elution with an eluting liquid, said thiophilic moieties comprising a two part structure wherein one part can be characterized as a hydrophilic electron acceptor and the other part is sulfur which acts as an electron donor; selecting a sample of a fluid biological material to be tested for PSA and its complexes; introducing the sample into the column; eluting the sample through the column; rinsing the column with adsorption liquid to remove materials that are unbound to the thiophilic gel; and capturing PSA and its complexes in eluted column fractions.

19 Claims, 9 Drawing Sheets

Chromatography of PSA (Sigma) on Thiophilic Gels

OTHER PUBLICATIONS

K. Shibata, et al., "Purification and Characterization of Prostate Specific Antigen from Human Urine", Biochimica et Biophysica Acta 1336, 425–433, 1997.

C. Stephan, et al., "ACT–PSA and Complexed PSA Elimination Kinetics in Serum After Radical Retropubic Prostatectomy: Proof of New Complex Forming of PSA After Release into Circulation", Urology 55, 4, 560–563, 2000.

M. Wang, et al., "A Simplified Purification Procedure for Human Prostate Antigen", Oncology 39, 1–5, 1982.

J. Wu, et al., "Purification of PSA–ACT Complex: Characterization of PSA–ACT Complex by Various Chromatographic Procedures", J. Clinical Lab Analysis 9:25–31, 1995.

W. Zhang, et al., "Purification and Characterization of Different Molecular Forms of Prostate–Specific Antigen in Human Seminal Fluid", Clin. Chem. 41, 11, 1567–1573, 1995.

* cited by examiner

METHOD FOR DETECTING PSA AND ITS MOLECULAR FORMS USING THIOPHILIC GEL

BACKGROUND OF THE INVENTION

This invention relates to prostate specific antigen (PSA) and its protein complexes as may be found in blood serum, ascites, tissues, tumors and seminal fluid.

Prostate cancer is one of the most frequently diagnosed cancers among U.S. men, and is the second most common male cancer and is a leading cause of male cancer related mortality. In the United States over 35,000 men die annually from prostate cancer. Since its discovery, prostate specific antigen (PSA) has become the most valuable tool for the diagnosis and management of prostate cancer.

PSA, a single chain glycoprotein of approximately 30 kDa, is a member of the human kallikrein gene family, which consists of $hKLK_1$, $hKLK_2$ and $hKLK_3$ (PSA). All three genes are clustered within 60-kb genome region on chromosome 19 Q13.3-q 13.4. The PSA gene has five exons and encodes a 237 amino acid mature protein which is secreted. PSA protein is glycosylated at a single site (asparagine 45). Each PSA molecule has six immunoreactive binding sites.

PSA is primarily produced by prostate epithelial cells and is secreted into seminal fluid to a high concentration. PSA at low concentrations has been found in endometrium, normal brain tissue, breast tumors, breast milk, adrenal neoplasm and renal cell carcinoma. PSA circulates in the serum as uncomplexed or free form and complexed or bound form. In the serum most of the PSA is complexed with $\alpha_1$-antichymotrypsin (ACT) (1,2); and $\alpha_2$-macroglobulin ($A_2M$) (3). A small portion of PSA is bound to $\alpha_1$-protease inhibitor (API). A complex between PSA and protein C-inhibitor (PCI) is present only in seminal plasma.

Despite the wide spread acceptance and use of serum PSA as a marker, for the early detection of prostate cancer, the specificity of this PSA test is relatively low. The yield of cancer in a screening population is only 22–30%; which means that 70–80% of all test results, indicating that a biopsy should be performed, are false positives. Progressively rising PSA levels above the "normal range" of 0–4 ng PSA/ml are one of the earliest signs of prostate cancer. As a regular screening for prostate cancer becomes the standard of care, improved specificity in detection of prostate cancer is needed to avoid costly, unnecessary biopsies. PSA is produced by malignant as well as by non-malignant prostate epithelial cells. Therefore, there is a substantial overlap in total PSA levels between men with prostate cancer, benign prostatic hyperplasia (BPH) and chronic prostatitis. Recently, the measurement of the ratio between total PSA and free PSA has been introduced as a useful clinical tool for the early detection of localized prostate cancer in order to increase reliability of the test.

Different commercial PSA immunoassays usually give different results in the same patients. This underscores the need to standardize PSA assays. It is particularly important that PSA immunoassays be standardized in the range of 0–10 ng PSA/ml, because this is the most critical range for a prostate cancer screening program.

The process of standardization of the PSA-immunoassays requires several steps: 1) a standard method for PSA isolation in its native forms must be defined, 2) a method to preserve native PSA for a reasonable period and 3) a serum based PSA standard is needed. This is essential because most of the clinical decisions for patient care are based upon measurement of serum PSA levels whereas most, if not all, PSA standards currently used are from a seminal plasma source. Additionally, recent data indicate that analytical characteristics of seminal fluid PSA differs from that of serum PSA. Current PSA immunoassays are designed to measure total PSA in the serum. To evaluate differences in such assays, one should use "serum standards" containing different proportions of free and complexed PSA and not free PSA obtained from seminal plasma. It has been proposed that only the complexed forms of PSA be used as the internal antigen calibrator for PSA immunoassays. However, at present, no such standards are available.

Current PSA quantitation methodology estimates either free PSA, total PSA or PSA that complexes with $\alpha_1$ anti-chymotrypsin (PSA-ACT). It, however, does not include other known complexes such as $\alpha_2$ macroglobulin complex with PSA (PSA-$A_2M$); $\alpha_1$-protease inhibitor complex with PSA (PSA-API) and a complex between PSA and protein C inhibitor present only in seminal fluid (PSA-PCI). This is the reason why total PSA determination is often higher than sum total of free PSA and PSA-ACT complex. In order to correctly define the role of different molecular forms of PSA in immunoassays it is essential that an entire panel of PSA molecular forms (free and complexed forms) found in the patient samples, e.g., serum, be represented in standardization of PSA assays and in preparation of a PSA calibrator.

All currently available methods for the quantitation of PSA involve use of monoclonal and polyclonal antibodies to measure free PSA and PSA-ACT complex, usually in the serum. Regardless of the assay procedure used, the value of total PSA always exceeds the sum of free PSA and PSA-ACT complex by up to 30%. Possible reasons for this discrepancy may be: 1) presence of other known PSA-complexes (PSA-$A_2M$, PSA-API), 2) other unknown PSA-complexes, 3) differences in specificity of anti-PSA antibodies-as they are prepared against free PSA from seminal plasma and may have different affinity for free PSA than PSA-complexes, 4) differences in the degradation rate of different PSA molecular forms, 5) use of seminal plasma based PSA as an internal antigen calibrator, 6) use of solid phase for immobilizing the capture antibody which may affect the kinetics of antigen-antibody interaction and 7) any combination of these.

For the most part, the source for the isolation of prostate specific antigen (PSA) for clinical and laboratory use has been seminal plasma and rarely from cultured prostate tumor cells. As of today, all internal standards used for monitoring PSA in patient serum are prepared from seminal plasma. However, the biochemical nature of PSA from seminal plasma and from patient blood may not be identical. Thus far no one has purified PSA or any of its molecular forms directly from the patient serum. Most identification of PSA in patient serum is based upon immunological detection and quantitation using monoclonal and polyclonal antibodies. The validity and accuracy of such measurements largely depends upon the quality and nature of each antibody used. There is no single antibody known today that can capture free PSA and all of its molecular forms.

Thiophilic adsorption chromatography was first introduced by Porath and coworkers in 1985 employing a thiophilic gel containing a sulfone group and at least one thioether function. The synthesis of the gel consisted of coupling 2-mercaptoethanol to agarose that has been activated by divinylsulfone. The adsorption of proteins to the stationary phase of their particular gel and many others is promoted by high concentration of lytropic-salts such as sodium, potassium and ammonium sulfates, whereas desorption is achieved by decreasing salt concentration. Thiophilic adsorption chromatography has been largely used for the purification of immunoglobulins of different classes: IgA, IgG and IgM from different species and for purification of polyclonal antibodies from serum and monoclonal antibodies from tissue cellular supernatants and from ascitic fluid. Ion exchange effects are excluded in view of high salt concentration in the adsorption step. There has, however, been no recorded indication or suggestion that thiophilic gels might have applicability to isolation or purification of PSA.

Thiophilic gels have pendant surface ligands attached to a hydrophilic solid support, e.g. agarose or polyacryamide. The surface structures are ligands containing hydrophilic electron donor and acceptor groups. Commercially there are three different thiophilic gels that contain one, two and three sulfur containing groups respectively.

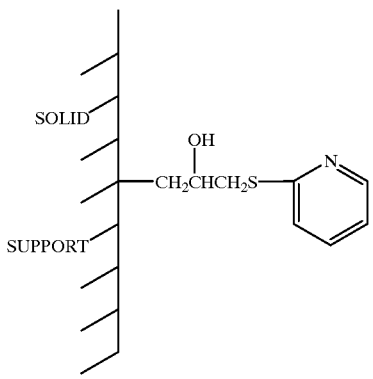

One Sulfur

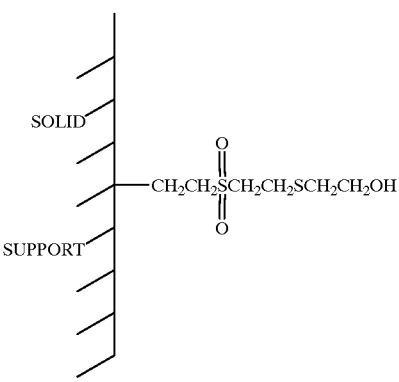

Two Sulfurs and

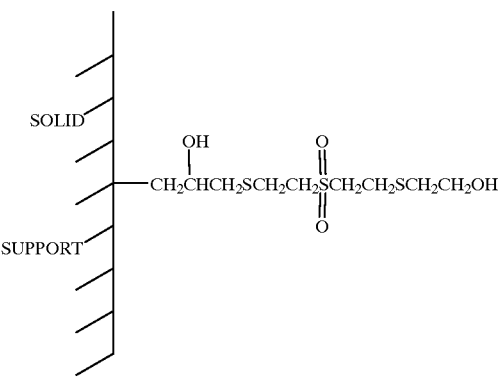

Three Sulfurs

The adsorption of proteins to T-gels is usually promoted by "structure forming" (lyotropic) salts. Typically, protein solutions are applied on T-gels at high salt, e.g. sulfate, concentration, about 0.5 to about 1.0 Molar, at about pH 6 to about pH 8, and adsorbed proteins are eluted by a decrease of salt concentration in the mobile phase.

BRIEF DESCRIPTION OF THE INVENTION

In accordance with the invention, it is therefore an object to provide a method for the isolation of PSA and its molecular forms, e.g. complexes or isoforms, from biological fluids.

It is a further object to isolate PSA and its molecular forms from biological fluids without using monoclonal or polyclonal antibodies.

It is a further object of the present invention to provide a method for isolation of PSA and its molecular forms that provides consistency in quantitative analysis of free PSA, complexed PSA and total PSA.

It is a further object of the present invention to provide a method to separate and quantify free PSA and its various molecular forms and to be able to use the ratios and quantities of free PSA and its various complexes to increase reliability of screening tests for prostate cancer.

It is a further object of the present invention to prepare PSA test standards based upon serum rather than upon seminal fluid as a source of PSA.

The foregoing and other objects of the invention are met by the discovery of a method for capturing and isolating PSA and all of its known complexes from biological fluids using thiophilic gels. Such captured and isolated PSA and PSA complexes can be then quantified by known methods.

The invention includes a method for capturing PSA and its molecular forms that may be in a fluid biological material including the steps of:

a) preparing a chromatographic column by placing a thiophilic gel in a column where the thiophilic gel is formed from a water insoluble polymer where the surface of the gel is provided with thiophilic moieties that bind PSA in the presence of an adsorption liquid but that will release PSA upon elution with an eluting liquid, said thiophilic moieties comprising a two part structure wherein one part can be characterized as a hydrophilic electron acceptor and the other part is sulfur which acts as an electron donor;

b) selecting a sample of a fluid biological material to be tested for PSA and its complexes;

c) introducing the sample into the column;

d) passing the sample through the column;

e) rinsing the column with adsorption liquid to remove materials that are unbound to the thiophilic gel;

f) eluting the column with a liquid that will displace PSA; and g) capturing PSA, including its complexes, in eluted column fractions.

More particularly, in a preferred embodiment, the method for capturing PSA including its complexes from fluid biological material includes the steps of:

a) preparing a chromatographic column by placing a thiophilic gel in a column where the thiophilic gel is selected from the group consisting of PyS, 2S and 3S;

b) equilibrating the column with an aqueous alkali metal sulfate salt solution at a concentration of from about 0.5 to about 1.0 Molar;

c) selecting a sample of a fluid biological material to be tested for PSA and its complexes;

d) adding alkali metal sulfate to the sample to obtain a salt concentration of from about 0.5 to about 1.0 Molar;

e) introducing the sample into the column;

f) eluting the column with an aqueous alkali metal sulfate salt solution at an original concentration of from about 1.0 molar to 0.5 Molar to remove materials that are not bound to the gel;

g) displacing proteins bound to the gel by rinsing the column with aliquots of aqueous solutions of alkali metal sulfate salt at concentrations incrementally reduced from the about 0.5 to about 0.1 original concentration to obtain column fractions; and h) analyzing the displaced proteins for PSA.

The invention further includes separation of PSA and its complexes by collecting column fractions and quantification of PSA or PSA complex in the fractions.

DETAILED DESCRIPTION OF THE INVENTION

Figure 1:
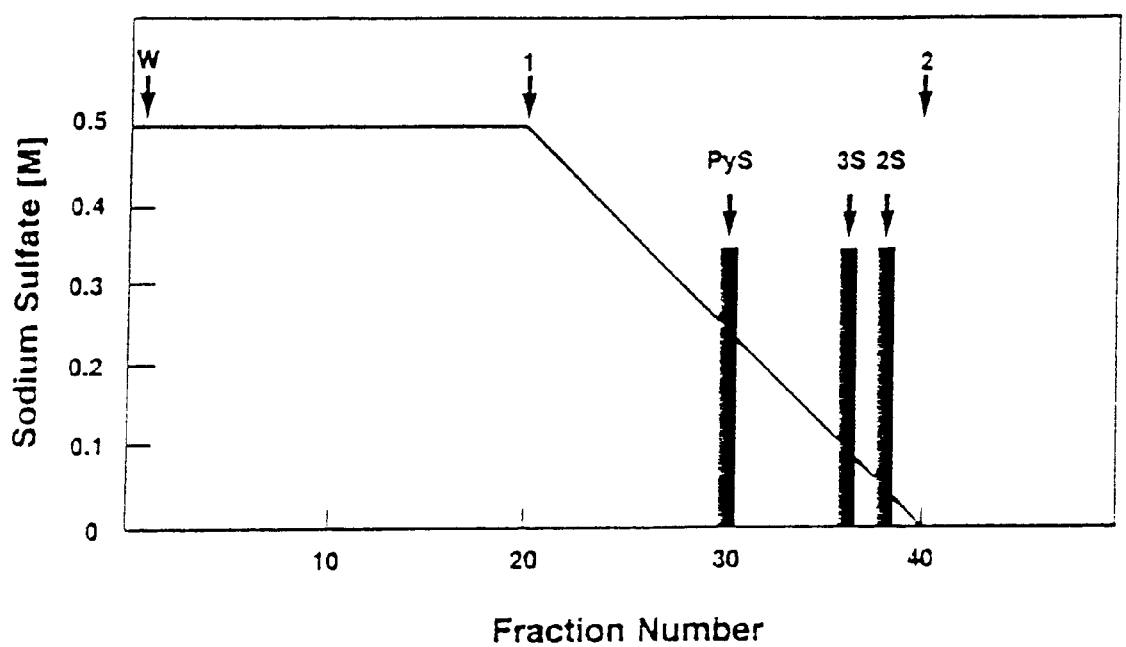
FIG. 1 shows a graph of sodium sulfate concentration versus PSA fraction number through columns containing different T-gels (PyS, 2S, and 3S). The graph shows that PSA was eluted from PyS at the highest salt concentration, 0.25M (weakest bound) and that PSA is released from 2S and 3S at a salt concentration of less than about 0.1M. The presence of PSA in the fractions was detected using anti-PSA antibody.

"Capturing PSA" as used herein means that PSA and its complexes are removed from a fluid biological sample by binding to a thiophilic gel. The captured PSA and complexes may later be eluted from the gel by means of salt solution applied at decreasing concentration or in the case of pH sensitive thiophilic gels, by means of a pH shift.

"PSA" is intended in its broad sense to include both free and complexed PSA.

"PSA Complex" is intended to include PSA that is complexed to another organic material, such as another protein, within a biological fluid.

"Biological fluid" is intended to mean any biological fluid, regardless of its source, that may contain PSA. Such fluids are intended to include, but are not limited to, seminal fluids, blood serum, ascites, excreted fluids such as urine and cellular fluids of both normal and cancerous tissue.

"Sample" is intended to include a testable quantity of any biological fluid that contains PSA.

"Thiophilic gel" means a gel formed from a hydrophilic high molecular weight water insoluble polymer where the surface of the gel is derivatized with thiophilic moieties that bind PSA but that will release PSA upon elution with water or dilute salt solution or in the case of a pH sensitive thiophilic gel with a drop in pH, e.g. from above about seven to below about five. The high molecular weight water insoluble hydrophilic material is usually a high molecular weight water insoluble polysaccharide such as agarose, a silanized silica or a polyacryamide.

The thiophilic moiety usually contains at least one thioether sulfur group and at least one electron donor group. The thioether sulfur group and electron donor group are usually separated by no more than two carbon atoms.

There are numerous thiophilic ligands that may be used in accordance with the invention, e.g. as described in Schwarz et al., *Possible Sites On Antibodies Involved in Thiophilic Adsorption*, Advances in Molecular and Cell Biology, v. 15b, pp. 547–551, 1996, incorporated by reference as background art. In general, such thiophilic ligands comprise a two part structure wherein one part can be characterized as a hydrophilic electron acceptor like sulfone or pyridine and. the other part is sulfur which acts as an electron donor. The two parts are appropriately spaced so as to specifically interact with aromatic structures on PSA at a particular pH or salt concentration. One especially interesting thiophilic ligand is mercaptoethylene-pyridine (MEP) which may bind with PSA at one pH, usually near physiological pH, e.g. pH about 7 and release it at a different pH below physiological pH, e.g. at a pH of about 4 to about 6. MEP sorbents, e.g. MEP HYPERCEL™, utilizes a hydrophobic tail and an ionizable head group in uncharged form. The heterocyclic head group, i.e. 4 mercaptoethyl pyridine (4-MEP) acts as an aromatic structure contributing to hydrophobic binding. The sulfur atom of 4-MEP contains a thioether and binds by thiophilic interaction. The MEP ligand is immobilized on solid matrix, e.g. 80–100 μm spheres, through a tail region by ether or thioether bonds. Most other thiophilic ligands require lyotropic salts, e.g. phosphates, sulfates, citrates or acetates, in a mobile phase for release of PSA. The preferred lyotropic salt is sodium sulfate. Preferred thiophilic gels (T-gels) are PyS, 2S, and 3S previously described. 2S and 3S are preferred over PyS due to their stronger binding of PSA.

The invention may be illustrated by, but is not to be limited by, the following examples. In the examples, unless otherwise indicated, all parts and percentages are by weight.

Clinical samples were obtained from Roswell Park Cancer Institute at Buffalo, N.Y. Seminal plasma samples were obtained from the fertility clinic at Children's Hospital, Buffalo, N.Y. All studies were carried out under approved protocol #CIC 99-09.

Thiophilic gels containing one sulphur (PyS T-gel) and two sulphurs (2S T-gel) were obtained from Sigma Chemical Co., St. Louis, Mo. Thiophilic gel containing three sulphurs (3S T-gel, FRACTOGEL-EMD/TA(S)) was obtained from EM Industries Inc., Gibbstown, N.J. These thiophilic ligands are referred to herein as T-gel (PyS), T-gel (2S) and T-gel (3S), respectively.

A T-gel slurry, prepared as previously described, was packed in a BIO-RAD column (0.5×10 cm) and equilibrated with 25 mM of Hepes buffer, containing 1M sodium sulfate, pH7.0. Test samples (commercial PSA, seminal plasma or patient serum) reconstituted in column equilibrating buffer was applied to the column. The column was then washed with approximately 10 void volumes with equilibrating buffer. Bound proteins were eluted either by developing a linear gradient of decreasing salt concentration or by stepwise elution using aqueous solutions having decreasing salt concentrations.

Two microliter aliquots of each of the test sample were spotted on a sheet of nitrocellulose membrane. After blocking the membrane with a solution of 1% albumin in 20 mM phosphate buffer containing 0.15M sodium chloride (PBS) for 30 minutes, it was exposed to an appropriate dilution of anti-PSA antibody (F-5, from American Type Culture Collection (ATCC) or A-6 from Santa Cruz Biotech, Calif.) for an additional 30 min. The membrane was washed 3 times with PBS containing 0.1% TWEEN-20 and then exposed to peroxidate-conjugated secondary antibody for 30 min. At the end of this incubation period, the membrane was washed three times and peroxidase activity was revealed using diaminobenzidine as a substrate in PBS, pH 7.2.

To identify PSA-complexes, PSA-ACT, PSA-PCI and PSA-A$_2$M, in the patient serum, in the seminal plasma or in various T-gel column eluates, a double determinant ELISA method was used. The following capture antibodies were used: monoclonal anti-$\alpha_1$-antichymotrypsin antibody (CalBiochem, San Diego, Calif.), monoclonal anti-PCI antibody (American Diagnostica Inc., Greenwich, Conn.) and polyclonal A$_2$M antibody (Sigma Chemical Co., St. Louis, Mo.). The detection antibodies were respectively: polyclonal rabbit anti-PSA antibody (DAKO Corp., Carpinteria, Calif.) for ACT and PCI complexes and monoclonal anti PSA (ATCC, Rockville, Md.) for A$_2$M complex. Microtiter plates were coated with appropriate dilutors of respective capture antibody in PBS overnight at 4° C. The plates were washed three times with PBS containing 0.01% TWEEN-20 (washing buffer) and blocked with 250 Ul of 2% bovine serum albumin (BSA) solution in PBS for 1 hr. All further steps were carried out at room temperature. Appropriate dilutions of each test sample (50 Ul) were added in duplicate to wells and incubated for 1 hr. For the detection, 50 μl of appropriately diluted detection antibody was added to each well and incubated for 1 hr. The plates were exposed to peroxidase-labeled secondary antibody (Jackson Labs, West Grove, Pa; 1:5000 dil) for 45 min. After washing the plates, 150 μl of the substrate solution containing 0.01% H$_2$O$_2$, 0.4 mg/ml of O-phenyldiamine in 0.2M citrate buffer, pH 5.0 was added to each well for 15 min. The reaction was stopped by addition of 50 μl of 2N sulphuric acid and the intensity of the color was measured at 490 nm in a plate reader.

Proteins were electrophoresed under nonreducing conditions through 4–15% gradient gel (Bio-Rad Labs, Hercules, Calif.) using the discontinuous procedure of Laemmli, Nature, Vol. 227, p 680 (1970) incorporated herein as background art. Proteins were then electrophoretically transferred to polyvinylidene difluoride (PVDF) paper with transfer buffer at pH 8.2. The blots were blocked at room temperature for 1 hour with a liquid containing a protein material such as 5% dry milk and 0.1% TWEEN 20 surfactant in PBS, e.g. NAP-SURE BLOCKER (Geno Technology, St. Louis, Mo.), and incubated with primary anti-PSA antibody for 1 hr at room temperature. After washing three times with PBS containing 0.1% TWEEN 20, the blots were incubated at room temp for 1 hour with peroxidase conjugated secondary antibody. After washing four times, the blots were developed using a chemiluminescence detection kit (Geno Technology) and recorded with KODAX X-OMAT-AR film.

Purified PSA, ACT and A$_2$M were purchased from Sigma. Ten micrograms of PSA was incubated with 10 ug of A$_2$M or 10 ug of ACT in PBS containing 0.1% albumin, pH 7.4 for 30 minutes at 37° C. The in vitro made complexes were used without further purification as a standard for the Western blot and subjected to chromatography on a T-gel column.

A Bio-Rad column (0.5×7 cm) was packed with T-gel slurries (PyS, 2S, and 3S) in 25 mM Hepes buffer containing 0.5M sodium sulfate, pH 7.0. Ten micrograms of PSA, obtained from Sigma Chemical Co., St. Louis, Mo., was reconstituted in 400 ul of column equilibrating buffer and applied to the column. The columns were washed with 20 ml of equilibrating buffer. The elution was carried out with a 20 ml of linear gradient of decreasing sodium sulfate concentration (0.5 to 0.0M) in 25 mM Hepes buffer, pH7.0 and followed with 10 ml of the terminal buffer. The flow rate was 0.166 ml/min and one ml fractions were collected. The presence of PSA in various column fractions was initially detected by dot-immunobinding assay using anti-PSA antibody (F5 or A6).

No PSA activity was detected in the wash region or in the terminal buffer region of the columns. Under applied chromatographic conditions, the PSA was selectively retained. The bound PSA was dislodged from the column when salt concentration was reduced to nearly 0.1M. The identity of PSA in various column fractions was further confirmed by SDS-PAGE and Western-blot analysis. The majority of the PSA was present in column fractions 32–40.

Similar results were obtained when PSA (Sigma) was chromatographed on T-gels (2S and 3S). However, the binding of PSA (Sigma) on T-gel (PyS) is considerably weaker since the bound PSA was eluted from the column when salt concentration was reduced from 0.5M to 0.25M. The relative elution characteristics of commercially available PSA from T-gel (PyS), T-gel (2S), and T-gel (3S) columns is shown in FIG. 1.

Figure 2:
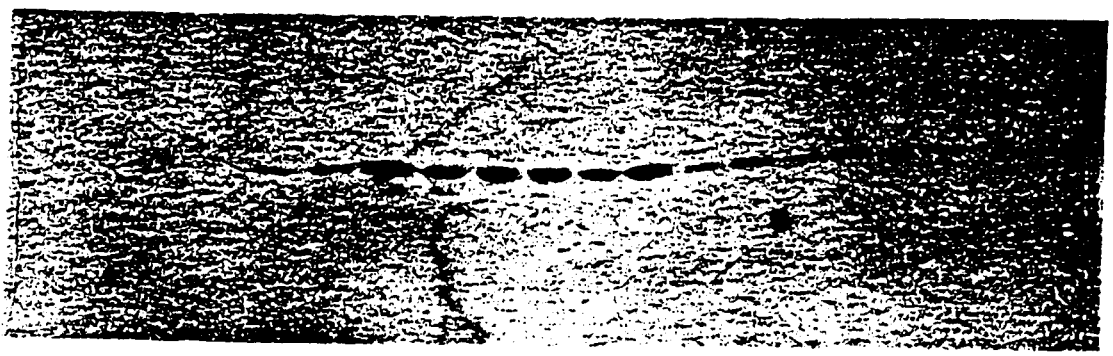
FIG. 2 shows a Western-blot analysis of commercial PSA chromatographed on T-gel 3 S.

FIG. 2 represents the SDS-PAGE and Western blot analysis of commercially available PSA (Sigma) chromatographed on T-gel ($S_3$). PSA was detected using monoclonal anti-PSA antibody (A6). The samples were run under non-reducing conditions on 4–15% SDS PAGE followed by electrophoretic blotting on PVDF membranes and detected by chemiluminescence. PSA is shown as a single band with molecular weight of approximately 33 kDa. The majority of PSA was detected in fractions 33 to 38 which corresponds to the peak elution of approximately 0.1M sodium sulfate.

No differences in chromatographic behavior were seen when PSA from other commercial sources (Calbiochem, San Diego, Calif., Chemicon International Inc., Temecula, Calif.) were chromatographed on all three types of T-gels.

Unless otherwise indicated, all subsequent experiments were carried out using T-gel (3S) preparations.

Figure 3:
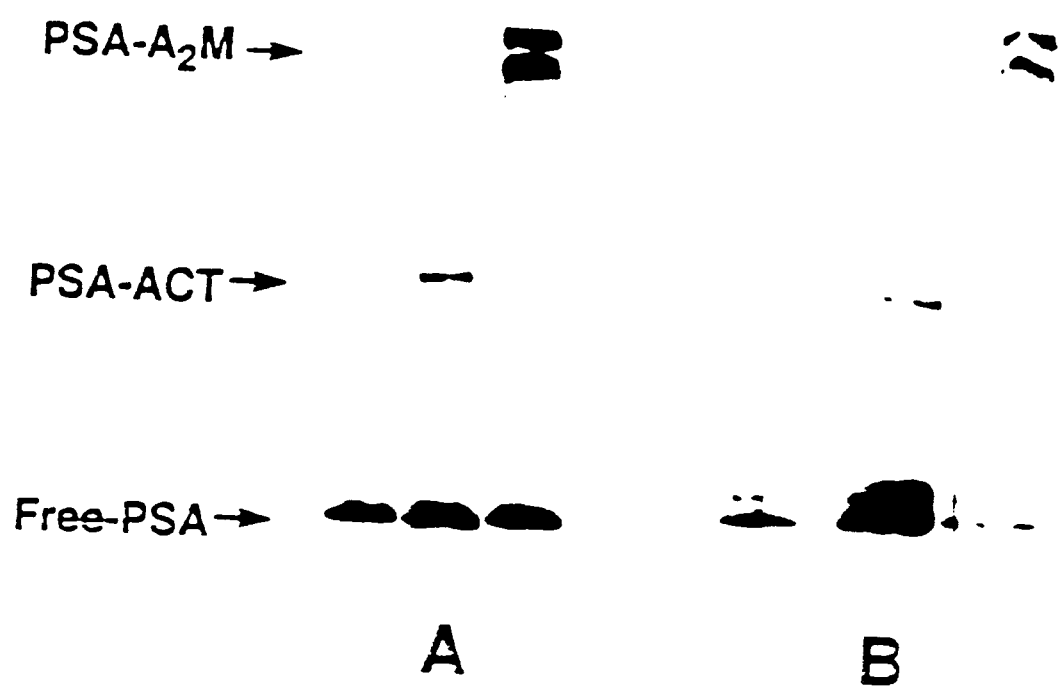
FIG. 3 shows SDS-PAGE and Western transfer of Free-PSA, PSA-ACT and PSA-$A_2M$ complexes before and after T-gel chromatography on T-gel 3S.

Affinity of in vitro made PSA-ACT and PSA-$A_2$M Complexes for T-gel (3S) was tested. Ten micrograms of PSA (Sigma) was incubated with 10 μg of $\alpha_1$-antichymotrypsin (ACT) or $\alpha_2$-macroglobulin ($A_2$M) in 20mM sodium phosphate buffer containing 0.1% albumin, pH 7.0 at 37° C. for 30 min. At the end of incubation, each sample was chromatographed separately in a T-gel (3S) column prepared as previously described. The bound material was eluted with 25 mM Hepes, pH 7.0 containing no sodium sulfate: The distribution of immunoreactive PSA was initially monitored for all column fractions using dot-immunobinding assay. No PSA was detected in initial column work regions or in terminal elution regions. Fractions containing PSA were further identified by SDS-PAGE and Western transfer and probed by anti-PSA antibody. Panel A of FIG. 3 shows; free-PSA, in vitro made PSA-ACT, and PSA-$A_2$M complexes analyzed prior to T-gel chromatography and Panel B shows; free-PSA, in vitro made PSA-ACT, and PSA-$A_2$M complexes analyzed after T-gel chromatography. The results clearly show T-gel has affinity for a spectrum of PSA complexes.

Tests were conducted to determine T-gel affinity for PSA and its complexes in seminal fluid. A sample of pooled seminal plasma was centrifuged at low speed (2000×g for 10 min) at 4° C. and the supernatant was dialyzed overnight against 20 mM phosphate buffer, pH7.0. The dialyzed seminal plasma was further clarified by centrifugation at 10,000×g for 20 min at 4° C., aliquoted and stored at −70° C. until used.

Figure 4:
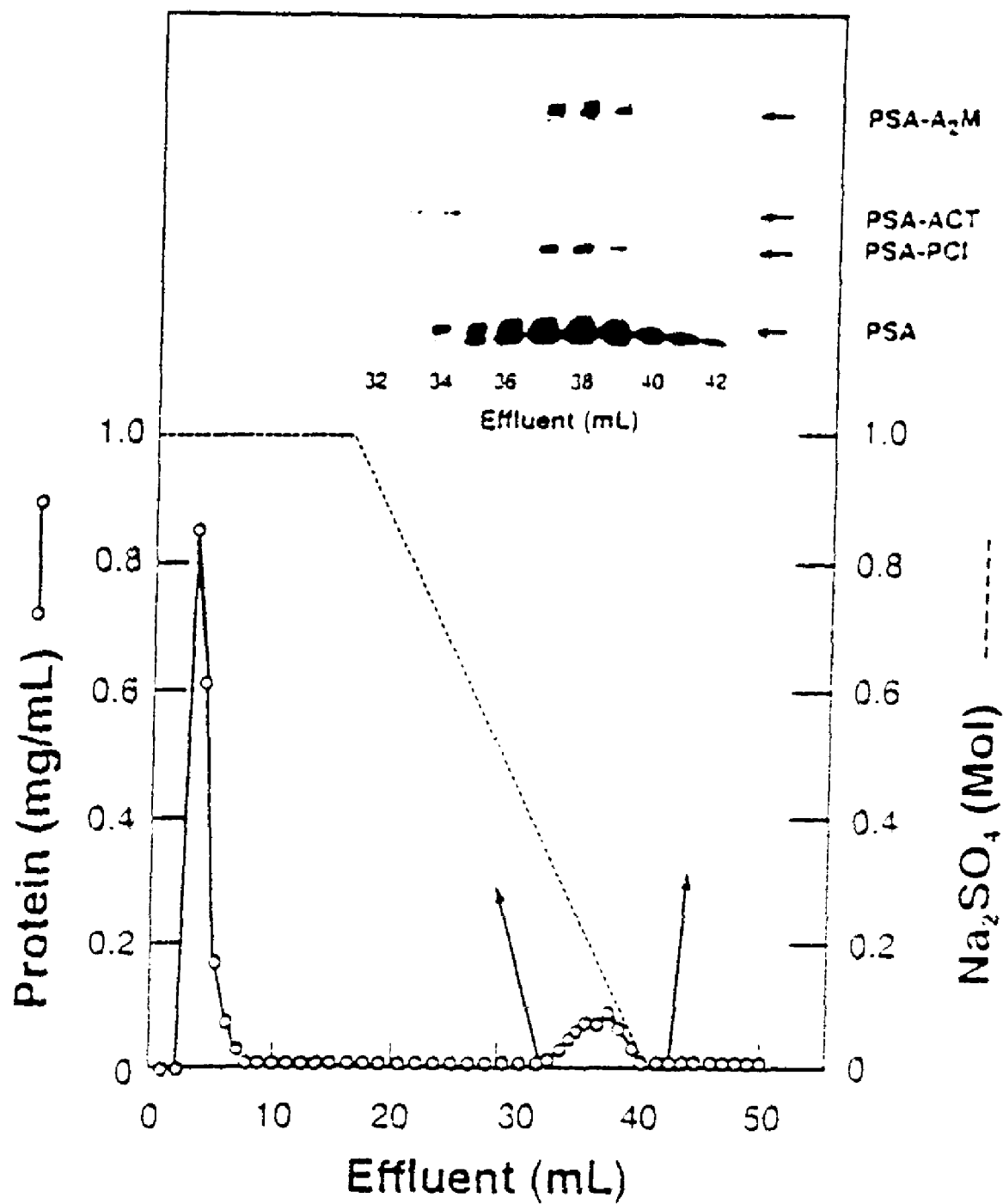
FIG. 4 shows a graph and SDS-PAGE Western blot transfer, using anti-PSA antibody, of protein concentration in effluent from a 3S T-gel column to which a dialyzed seminal plasma sample was applied.

A sample of seminal plasma was mixed with equal volume of 2X column equilibration buffer and applied to T-gel (3S) column equilibrated with 25 mM Hepes containing 1M sodium sulfate, pH.7.0. After washing the column with column equilibration buffer, the bound proteins were eluted by developing a linear gradient of decreasing salt concentration, as described earlier. The presence of PSA in the column fractions was initially monitored by dot-immunoblotting assay. No PSA was detected in the wash or terminal buffer region of the column. Protein concentration was evaluated using bicinchoninic acid (BCA) protein assay reagents (Pierce, Rockford, Ill.) and used with 96 well microtiter plates. All fractions in the gradient region with PSA immunoreactivity were further analyzed by SDS-PAGE and Western blotting using anti-PSA antibody. The results are shown in FIG. 4. Free PSA and three complexed PSA's were detected in the gradient region of the column. According to immunostaining, PSA-$A_2$M is the predominant complex in the seminal plasma followed by PSA-PCI. PSA-ACT complex was detectable but at a low concentration, as judged by the intensity of the stained gels.

Figure 5:
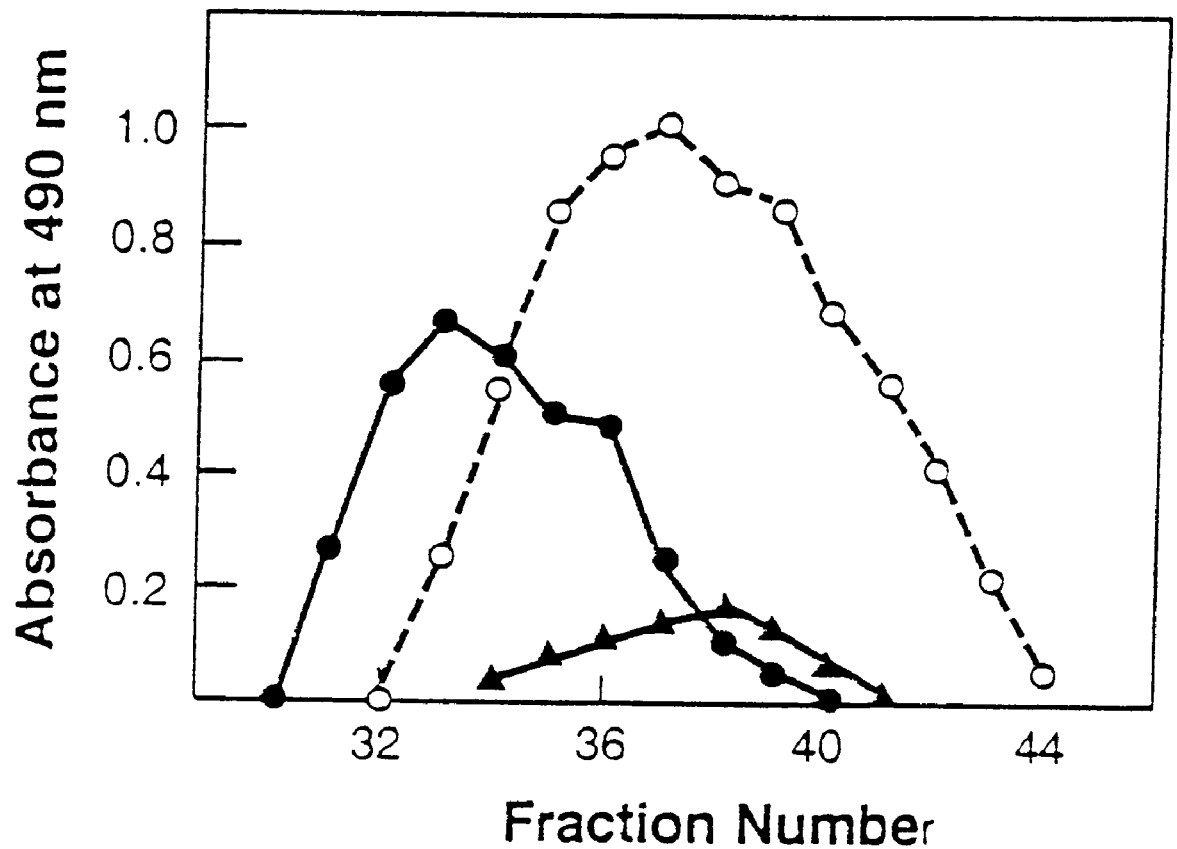
FIG. 5 shows a graph of an ELISA analysis of column fractions of seminal plasma through a 3S T-gel column.

In addition to immunostaining, the same column fractions were also analyzed for various PSA-complexes by double determinant-ELISA (FIG. 5). In contrast to immunostaining, the predominant form of the complex in ELISA determination was PSA-PCI complex followed by PSA-ACT complex. The PSA-$A_2$M complex was barely detectable. The results indicate that only trace quantities of % PSA complexed to $A_2$M is detectable in ELISA for total PSA.

Figure 6:
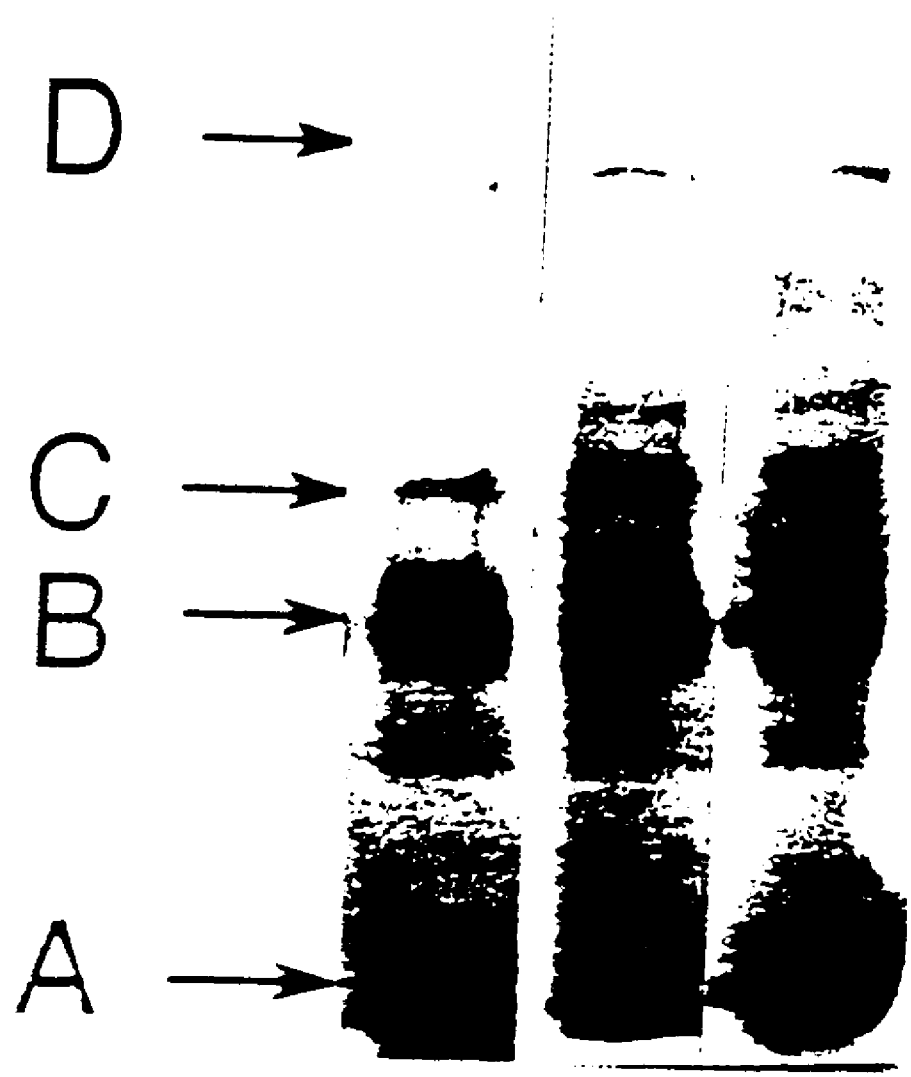
FIG. 6 shows an SDS-PAGE and Western blot of seminal plasma processed through T-gel columns of PyS, 2S and 3S illustrating lower gel affinity for PSA and its complexes in a PyS column.

In separate series of experiments, the chromatographic behavior of PSA and its molecular forms present in the seminal plasma were compared on T-gel (PyS), T-gel (2S), and T-gel (3S) columns. Identical samples of seminal plasma were applied to each of the column and columns were developed as described for FIG. 4. Fractions that were immunoreactive for PSA were pooled and analyzed by SDS-PAGE and Western blot. Initially the blots were stained with monoclonal PSA-antibody (A6). There were no apparent differences in the pattern of PSA-molecular forms as revealed in the blots. Four molecular forms of PSA were identified for each column by staining the blots with corresponding antibody: A, Free PSA; B, PSA-PCI, C, PSA-ACT and D, PSA-$A_2$M. The numbers 1, 2 & 3 represent T-gel (PyS), T-gel (2S) and T-gel (3S) respectively. The identity of each PSA-complex was also confirmed by staining the duplicate gels respectively with anti-$A_2$M, anti-ACT and anti-PCI antibodies. The results are shown in FIG. 6.

Serum from a healthy female does not contain any detectable amounts of free or complexed forms of PSA. Normal human sera, both male and female, are known to have abundant quantities of $\alpha_1$-antichymotrypsin (0.5 mg/ml) and $\alpha_2$-macroglobulins (3 mg/ml). Female serum when spiked with free PSA is known to produce complexed isoforms. PSA-ACT and PSA-$A_2$M complexes have been previously identified in spiked female serum.

200 microliters of female serum was spiked with 5 μg of free PSA, incubated for 1 hr at 37° C. and immediately chromatographed on a T-gel ($S_3$) column as described with respect to FIG. 3. After washing the column with column equilibrating buffer, PSA retained on T-gel column was eluted with 25 mM Hepes buffer, pH7.0 without any salt (one step elution). In our experience this "one step" elution procedure provides large amounts of PSA in relatively small volume.

Figure 7:
FIG. 7 shows a Western-blot of eluent from a 3S T-gel column to which 200 microliters of female serum spiked with 5 μg of free PSA had been applied. The blot shows that PSA-$A_2M$ and PSA-ACT complexes had formed in the serum. The blot shows that a majority of the free PSA had been converted to PSA-$A_2M$ complex.

The identities of PSA and its molecular forms were confirmed by immunostaining after SDS-PAGE and Western transfer with anti-PSA antibody (A6). The results are shown in FIG. 7. Free PSA and two complexes—PSA-ACT and PSA-$A_2$M—were identified. After one hour of incubation, the majority of free PSA added to the female serum was converted to $A_2$M complex as is evident from FIG. 7.

Figure 8:
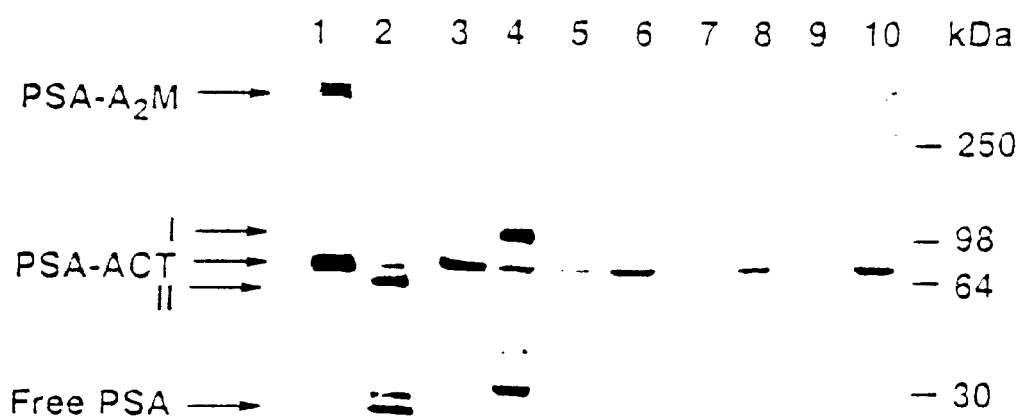
FIG. 8 shows SDS-PAGE and Western blot of fractions of a 3S T-gel column after application of 400 μl of serum from a patient having prostate cancer. The blot shows free PSA, two known complexes (PSA-ACT and PSA-$A_2M$), and two unknown complexes (I & II). "

Serum samples were obtained from 24 patients. Three of these patients were $T_1$, (located solely within prostate with no symptoms, too small to be felt); 10 of $T_2$ (located solely within prostate, large enough to be felt); 5 of $T_3$ (tumor spread into tissues immediately surrounding the prostate); 1 of $T_4$ (tumor within pelvic region); and 5 with late stage metastatic disease according to the tumor-nodes-metastatic clarification of IUAC. In addition to these cancer patients, sera from four normal healthy individuals and two chronic prostatitis patients were also included. A sample (400μl) of the serum was applied to the T-gel (3S) column. The column was developed according to the procedure for FIG. 4. No PSA was detected in the breakthrough or terminal region of the column for any of the patient serum processed through thiophilic gel. A total of 24 patient sera were processed. The fractions containing PSA were analyzed by SDS-PAGE and Western-blotting using anti-PSA antibody (A6). Immunostaining with anti PSA-antibody showed anywhere between 1 to 4 PSA-isoforms in different patient sera. The results from eight patients and two controls are presented in FIG. 8. Two of these patients (#1 and #4) with most advanced metastatic disease have detectable levels of PSA-$A_2M$ complex. Patient #4 with very high levels of c-PSA (>2000 ng/ml) has an additional unidentified PSA complex (FIG. 8, I) with molecular weight higher than PSA-ACT complex. Patient #2 with $T_1C$ stage of the disease having elevated total PSA and very low c-PSA (0.22 ng/ml) has also an additional unidentified PSA-complex that is lower in molecular weight than PSA-ACT complex (FIG. 8, II). Nearly all patients have PSA-ACT complex. The distribution of PSA and its isoforms, as seen in different patient serum, is perhaps the reflection of different stages of the disease.

Figure 9:
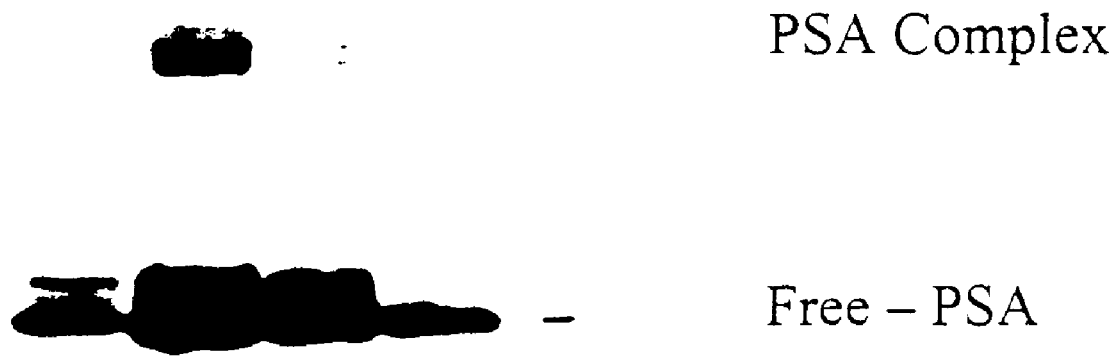
FIG. 9 shows an SDS/Page Western blot of chromatographed seminal plasma containing PSA immunostained with anti-PSA antibody."

In a further example one ml of seminal plasma containing PSA was chromatographed on MEP HYPERCEL™ sorbent (BioSepra, Life Technologies, Inc. Rockville, Md) packed in a PHARMACIA™ column (0.9×5 cm) and equilibrated with 50 mM of Tris. HCL 8.0 buffer. The column was washed with 25 ml of column equilibrating buffer. The bound proteins were eluted with 20 ml of 50 mM of sodium acetate buffer, pH 4.0. The column eluates were subjected to SDS/PAGE Western-blot analysis and immunostained with anti-PSA antibody. Results presented in FIG. 9 clearly show that PSA and complexed PSA are retained on this ligand.

What is claimed is:

1. A method for capturing PSA and its molecular forms that may be in a fluid biological material including the steps of:
   a) preparing a chromatographic column by placing a thiophilic gel in a column where the thiophilic gel is formed from a water insoluble polymer where the surface of the gel is provided with thiophilic moieties that bind PSA in the presence of an adsorption liquid but that will release PSA upon elution with an eluting liquid, said thiophilic moieties comprising a two part structure wherein one part can be characterized as a hydrophilic electron acceptor and the other part is sulfur which acts as an electron donor;
   b) selecting a sample of a fluid biological material to be tested for PSA and its complexes;
   c) introducing the sample into the column;
   d) passing the sample through the column;
   e) rinsing the column with adsorption liquid to remove materials that are unbound to the thiophilic gel;
   f) eluting the column with a liquid that will displace PSA; and
   g) capturing PSA, including its complexes, in eluted column fractions.

2. The method of claim 1 wherein PSA and its complexes are separated within the column fractions.

3. The method of claim 1 wherein the thiophilic moiety contains at least eight carbon atoms and the electronegative group is selected from the group consisting of aliphatic sulfonyl and o-pyridinyl.

4. The method of claim 1 wherein the thiophilic moiety also contains at least one hydroxy group.

5. The method of claim 1 wherein the thiophilic moiety is selected from the group consisting of o-(2-hydroxybutylenemercapto)pyridine, butyleneoxyethylene (2-hydroxyethylmercaptoethylene)sulfone, and 2-hydroxybutylenemercapto-ethylene (2-hydroxyethylmercaptoethylene)sulfone.

6. The method of claim 1 wherein the biological sample is seminal fluid.

7. The method of claim 1 wherein the biological sample is serum.

8. The method of claim 1 wherein the biological sample is a culture medium.

9. The method of claim 1 wherein the biological sample is ascites.

10. The method of claim 1 wherein the column fractions are analyzed by SDS-PAGE.

11. The method of claim 1 wherein the column fractions are analyzed by ELISA.

12. The method of claim 1 wherein the thiophilic ligand is mercaptoethylene pyridine and the eluting liquid is water acidified to a pH of from about 4 to about 6.

13. A method for capturing PSA and its complexes from fluid biological material includes the steps of:
   a) preparing a chromatographic column by placing a thiophilic gel in a column where the thiophilic gel is selected from the group consisting of PyS, 2S and 3S;
   b) equilibrating the column with an aqueous alkali metal sulfate salt solution at a concentration of from about 1.0 to about 0.5 Molar;
   c) selecting a sample of a fluid biological material to be tested for PSA and its complexes;
   d) adding alkali metal sulfate to the sample to obtain a salt concentration of from about 1.0 to about 0.5 Molar;
   e) introducing the sample into the column;
   f) eluting the column with an aqueous alkali metal sulfate salt solution at an original concentration of from about 1.0 to about 0.5 Molar to displace materials that are not bound to the gel;
   g) displacing proteins bound to the gel by rinsing the column with aliquots of aqueous solutions of alkali metal sulfate salt at concentrations incrementally reduced from the about 1.0 to about 0.5 original concentration to obtain column fractions; and
   h) analyzing the displaced proteins for PSA.

14. The method of claim 13 wherein PSA and its complexes are separated within the column fractions.

15. The method of claim 13 wherein the thiophilic moiety contains at least eight carbon atoms and the electron acceptor is selected from the group consisting of aliphatic sulfonyl and o-pyridinyl.

16. The method of claim 13 wherein the thiophilic moiety also contains at least one hydroxyxl group.

17. The method of claim 13 wherein the moiety is selected from the group consisting of o-(2-hydroxybutylenemercapto)pyridine, butyleneoxyethylene (2-hydroxyethylmercaptoethylene)sulfone, and 2-hydroxybutylenemercapto-ethylene (2-hydroxyethylmercaptoethylene)sulfone.

18. The method of claim 13 wherein the column fractions are analyzed by SDS-PAGE.

19. The method of claim 13 wherein the column fractions are analyzed by ELISA.

* * * * *